United States Patent [19]

Gilis et al.

[11] Patent Number: 5,681,582
[45] Date of Patent: Oct. 28, 1997

[54] EXTENDED RELEASE, FILM-COATED TABLET OF ASTEMIZOLE AND PSEUDOEPHEDRINE

[75] Inventors: Paul Marie Victor Gilis, Beerse; Eugene Marie Jozef Jans, Meerhout; Guido Jozef Maria Gijs, Arendonk, all of Belgium

[73] Assignee: Janssen Pharmaceutica N.V., Beerse, Belgium

[21] Appl. No.: 545,830

[22] PCT Filed: Jun. 7, 1994

[86] PCT No.: PCT/EP94/01878

§ 371 Date: Nov. 8, 1995

§ 102(e) Date: Nov. 8, 1995

[87] PCT Pub. No.: WO94/28880

PCT Pub. Date: Dec. 22, 1994

[30] Foreign Application Priority Data

Jun. 14, 1993 [EP] European Pat. Off. ............ 93201697

[51] Int. Cl.$^6$ ............................................. A61K 9/20
[52] U.S. Cl. .................... 424/468; 424/469; 424/470; 424/472; 424/474; 424/480; 424/476
[58] Field of Search .................... 424/468, 469, 424/470, 472, 474, 480, 476

[56] References Cited

U.S. PATENT DOCUMENTS

| 4,369,172 | 1/1983 | Schor et al. | 424/19 |
| 4,829,064 | 5/1989 | Sunshine et al. | 514/255 |
| 4,975,426 | 12/1990 | Sunshine et al. | 514/159 |
| 4,996,061 | 2/1991 | Webb et al. | 424/475 |
| 4,999,226 | 3/1991 | Schock et al. | 424/472 |

*Primary Examiner*—Frederick Krass
*Attorney, Agent, or Firm*—Charles J. Metz

[57] ABSTRACT

The present invention is concerned with an extended release, film coated tablet comprising as active ingredients the antihistaminic, antiallergic agent astemizole and the adrenergic, decongestant agent pseudoephedrine hydrochloride and with a process of preparing such tablets.

9 Claims, No Drawings

EXTENDED RELEASE, FILM-COATED TABLET OF ASTEMIZOLE AND PSEUDOEPHEDRINE

CROSS-REFERENCE TO RELATED APPLICATIONS

This application is based upon PCT Application Serial No. PCT/EP 94/01878, filed Jun. 7, 1994, which claims priority from European Patent Application Ser. No. 93.201.697.5, filed on Jun. 14, 1993.

The present invention is concerned with an extended release, film coated tablet comprising as active ingredients the antihistaminic, antiallergic agent astemizole and the adrenergic, decongestant agent pseudoephedrine hydrochloride and also with a process of preparing such tablets.

The antihistaminic antiallergic agent astemizole, its preparation and activity are known from U.S. Pat. No. 4,219,559. The pharmacokinetics of astemizole in man, in particular its rapid distribution to tissues and its terminal half-life of about 1 day, are known from Drug Dev. Res., 8 (1–4), 71–78, 1986. Pseudoephedrine, and especially its hydrochloride salt is a known decongestant having a half-life of several hours, typically about 6 to 8 hours. It is therefore usually employed in divided doses of 60 mg three or four times daily or in sustained release preparations, usually in doses of about 120 mg every 12 hours.

An effective treatment of patients suffering from allergic disorders such as allergic rhinitis, perennial rhinitis and the like, calls for a composition that upon adminstration releases an antihistaminic agent and a decongestant in such a manner that effective plasma levels of both active ingredients are maintained throughout the next 24 hours, i.e. until the next administration.

The present invention deals with such a composition that comprises (i) astemizole which has a terminal half-life of about 24 hours and a rapid distribution and thus does not need any special precautions, together with (ii) pseudoephedrine hydrochloride that has too short a half-life to attain effective plasma levels for the desired 24 hours and therefore requires special technical measures.

In particular the composition of the present invention concerns a tablet comprising (a) an extended release matrix core comprising pseudoephedrine hydrochloride as the active ingredient, a highly viscous hydrophilic polymer as matrix material, a solid diluent and optitionally other formulating agents known in the art such as, for example, granulating agents, glidants, tablet binding agents, solvents, anti-caking agents, preservatives or lubricants;

(b) an extended release coating;

(c) a drug coating comprising astemizole and pseudoephedrine hydrochloride as active ingredients, a hydrophilic polymer and optionally other formulating agents known in the art such as surfactants, plasticizers, lubricants; and (d) a seal coating.

Said tablets preferably comprise about 75% of the available pseudoephedrine hydrochloride in the core from which it will be released over an extended period, and the remaining 25% in the drug coating which will be released and taken up together with the antihistaminic astemizole immediately following digestion.

The tablets comprise from 60 mg to 240 mg pseudoephedrine hydrochloride in the core, from 20 mg to 80 mg pseudoephedrine hydrochloride in the drug coating as well as 5 mg to 20 mg astemizole in said drug coating. Tablets for adult humans preferably comprise about 180 mg pseudoephedrine hydrochloride in the core, about 60 mg pseudoephedrine hydrochloride in the drug coating, and about 10 mg astemizole in the drug coating. Tablets for humans having a lower bodyweight, e.g. children are preferably only half as large and thus comprise about 90 mg pseudoephedrine hydrochloride in the core, about 30 mg pseudoephedrine hydrochloride in the drug coating, and about 5 mg astemizole in the drug coating.

The highly viscous hydrophilic polymer in the core of the tablet should release the active ingredient therein gradually, preferably with zero order release kinetics. Suitable highly viscous polymers have a viscosity ranging from about 3.500 mPa·s to about 100.000 mPa·s, in particular ranging from about 4.000 mPa·s to about 20.000 mPa·s. Examples of such polymers are hydroxypropyl methylcellulose, hydroxypropyl cellulose and hydroxyethyl cellulose. For the active ingredient pseudoephedrine hydrochloride this can conveniently be achieved using a hydroxypropyl methylcellulose having a viscosity of about 15 centistokes (15.000 mPa·s), e.g. hypromellose 2208, or using a hydroxypropyl cellulose polymer having a viscosity of about 4.000 to 6.000 mPa·s. The quantity of hydrophilic polymer necessary in the core depends on both the amount of pseudoephedrine hydrochloride therein and the viscosity of the polymer. More polymer is needed as the amount of pseudoephedrine hydrochloride increases and/or the viscosity is reduced. The quantity of hydroxypropyl methylcellulose (15.000 mPa·s) used can range from about 50% to about 90% by weight of the amount of pseudoephedrine hydrochloride, and preferably is from about 60% to about 75%.

The solid diluent in the core of the tablet can be selected from soluble diluents, for example sucrose, lactose, trehalose, maltose, mannitol, sorbitol, starches (corn, wheat, maize, rice, potato), starch hydrolysates, microcristalline starches, pregelatinized starch, and also from insoluble diluents, for example, dicalcium or tricalcium phosphate. It is preferably lactose and its amount can range from about 75% to about 85% by weight of the pseudoephedrine hydrochloride used.

Among the optional formulating agents that further may be comprised in the core of the tablet there may be mentioned agents such as polyvidone having suspending and dispersing properties and also, as in the present composition, useful tablet binding and granulating properties; solvents, in particular those used during the preparation, e.g. water and lower alcohols such as ethanol and isopropanol; glidants such as colloidal silica; lubricants such as magnesium stearate and/or palmitate, stearic acid; antiadherents such as talc and corn starch.

In the present tablets the amount of polyvidone may range from 2% to 6% and in particular is about 5%; the amount of glidant may range from 0.5% to 1% and the amount of lubricant may range from 1.5% to 4% (all percentages are by weight of the amount of pseudoephedrine hydrochloride used in the core).

The extended release coating covering the core of the tablet should be designed in such a manner that it releases the contents slowly, in particular that it does not release the contents of the core until the initial dose of pseudoephedrine hydrochloride in the drug coating has been released. By using an initial, fast release of pseudoephedrine hydrochloride from the coating followed by a sustained pseudoephedrine release from the core, effective pseudo-ephedrine plasma concentrations are reached within one hour and are maintained for about 24 hours. Preferably, the extended release coating comprises ethylcellulose together with a low viscosity hydroxypropyl cellulose or hydroxypropyl methylcellulose, e.g. hypromellose 2910 5 mPa•s and optionally a plasticizer such as polyethylene glycol, e.g. PEG 400. The ratio ethylcellulose: hydroxypropyl methylcellulose: plasticizer may range from about 7:3:2 to about 9:1:2 and preferably is about 4:1:1. The amount of extended release coating typically ranges from about 2% to about 3% by weight of the total core weight, preferably from about 2.5% to about 2.75%.

The drug coating comprises the active ingredients astemizole, preferably micronized, and pseudoephedrine hydrochloride in the amounts mentioned hereinbefore suspended in a low viscosity hydrophilic polymer such as hydroxypropyl methylcellulose, e.g. hypromellose 2910 5 mPa•s, and a surfactant such as a polyoxyethylene derivative of a sorbitan ester, e.g. polysorbate 20, polysorbate 40, polysorbate 60 or polysorbate 80. Among the optional formulating agents that further may be used in the drug coating there may be mentioned plasticizers such as polyethylene glycol, e.g. PEG 400 and other formulating agents known in the art.

The amount of hydrophilic polymer used in the drug coating should be kept to a minimum in order to limit the tablet size and the manufacturing effort. On the other hand, it should be sufficient to effectively coat the active ingredients astemizole and pseudoephedrine hydrochloride for immediate release onto the extended release core. Said amount can range from about 6 to about 10 mg per mg of astemizole and preferably is about 7 mg per mg of astemizole (or total drug amount: polymer satisfactorily is about 1:1). Plasticizer and surfactant are present in amounts of about 1 mg to 2 mg, respectively 0.025 to 0.035 mg, per mg of astemizole.

The seal coating comprises a hydrophilic polymer such as hydroxypropyl methylcellulose, e.g. hypromellose 2910 5 mPa•s and a plasticizer such as propylene glycol in a ratio 4: 1. The seal coating may optionally be opacified for example with a pigment such as titanium dioxide. The seal coating not only prevents loss of the drugs for immediate release by abrasion, but also improves shelf-life (stability) and in particular the organoleptic properties of the tablet.

The preferred tablets comprise approximately
(a) in the core
  180 mg pseudoephedrine hydrochloride
  142.65 mg lactose
  9 mg polyvidone
  1.35 mg colloidal silica
  117 mg hypromellose 2208 15000 mPa•s
  4.5 mg magnesium stearate
(b) in the extended release coating
  8 mg ethylcellulose 20 mPa•s
  2 mg hypromellose 2910 5 mPa•s
  2 mg PEG 400
(c) in the drug coating:
  60 mg pseudoephedrine hydrochloride
  10 mg astemizole microfine
  70 mg hypromellose 2910 5 mPa•s
  16.8 mg PEG 400
  0.3 mg polysorbate 80; and
(d) in the seal coating:
  8 mg hypromellose 2910 5 mPa•s
  2 mg propylene glycol.

The tablets according to the present invention can conveniently be prepared in the following manner.

The core of the tablet is prepared by thoroughly mixing pseudoephedrine hydrochloride with the solid diluent, preferably lactose. The mixture is introduced in a fluidized bed granulator (e.g. Glatt type WSG-30) and mixed further until homogeneous. A granulating liquid consisting of water, an alcohol such as isopropanol and a granulating agent such as polyvidone K 90 is sprayed on the mixture, employing an atomizing air pressure set near to maximum levels. The dry granules are sieved through a suitable screen. The hydrophilic polymer, preferably hypromellose 2208 15000 mPa•s and the glidant colloidal silica are also sieved and are thoroughly mixed with the granulate. The lubricant then is added and the mixture is well blended until homogeneous. The mixture is compressed to white tablets.

The extended release coating is prepared by slowly adding ethylcellulose 20 mPa•s and hypromellose 2910 5 mPa•s to a solution of ethanol, dichloromethane and plasticizer, and stirring until complete dissolution. The tablet cores are charged into a coating pan (e.g. Glatt type GC-750) and warmed with air to an outlet-air temperature of about 35° C.–40° C. The extended release coating solution is applied to the cores by means of a spray worked by air pressure. Upon completion, the coated cores are dried with dry air.

The drug coating is prepared by slowly adding the hydrophilic polymer, the plasticizer and the surfactant to a stirred and warmed amount of water. Consecutively there is further added water and both active ingredients and the suspension is homogenized. The mixture is allowed to cool to ambient temperature while stirring. The coated cores are charged into a coating pan and warmed with air to an outlet-air temperature of about 45° C.–50° C. The drug coating suspension is sprayed onto the coated cores and upon completion, the drug coated tablets are dried with dry air.

The seal coating is prepared by adding to a stirred and heated amount of water, the hydrophilic polymer and the plasticizer. More water is added and the solution is allowed to cool to ambient temperature. The drug coated tablets are charged into a coating pan and warmed with air to an outlet-air temperature of about 45° C.–50° C. The seal coating solution is sprayed onto the drug coated tablets and upon completion the finished tablets are dried with dry air. The coated tablets should be packed into containers impervious to water vapour, e.g. blister packs (alu-alu; PVDC, PE, PVC-alu).

Using the process parameters described above, a convenient, reproducible manufacturing method for preparing extended release, film coated tablets of astemizole and pseudoephedrine hydrochloride can be obtained. Pharmacokinetic studies show that the thus obtained tablets upon ingestion give rise to an immediate release of astemizole and the 25% pseudoephedrine hydrochloride present in the drug coating, followed by zero-order release of pseudoephedrine hydrochloride from the extended release matrix core. Effective plasma levels of both active ingredients are maintained for at least 24 hours.

EXAMPLE a) Preparation of tablet core.

In a planetary mixer there were mixed 12.6 kg pseudoephedrine hydrochloride and 9.986 kg lactose. The mixture was introduced in a fluidized bed granulator, mixed again and sprayed with a solution of 315 g polyvidone K90 in 2.03 l water and 4.76 l isopropanol at an atomizing air pressure of about 0.35 MPa. The granulate was dried by further supplying dry air. The dried granulate was sieved in an oscillating sieve (sieve mesh opening 1 mm). Hypromellose 2208 15000 mPa•s (8.19 kg) and colloidal silica (Aerosil®, 94.5 g) were sieved under similar conditions and mixed with the granulate in a planetary mixer until homogeneous. Magnesium stearate (315 g) was added and mixed thoroughly therewith. The granulate was then compressed in a rotatory press (Korsch PH 106) to 70,000 white tablets of 450 mg each.

b) Preparation of extended release coating solution

A stainless steel vessel was charged with 11.01 kg ethanol, 7.315 kg dichloromethane and 154 g PEG 400. While stirring, there was slowly added ethylcellulose 20 mPa·s (616 g) and hypromellose 2910 5 mPa·s (154 g).

c. Preparation of the drug coating suspension

Water (35.007 kg) was heated to about 70° C. and thereto were added slowly and while stirring hypromellose 2910 mPa·s (5.39 kg), PEG 400 (1.294 kg) and polysorbate 80 (23.1 g). Water (17.503 kg) was added, followed by the slow addition of pseudoephedrine hydrochloride (4.62 kg) and astemizole microfine (770 g). The suspension was homogenized and allowed to cool to room temperature while stirring continuously.

d. Preparation of the seal coating solution

Water (3.593 kg) was heated to about 70° C. and thereto were added hypromellose 2910 5 mPa·s (616 g) and propylene glycol (154 g). Water (1.797 kg) was added and the mixture was stirred until complete dissolution.

e. Coating of the tablet core

The tablet cores were placed in the coating pan (Glatt GC 750) and heated with warm air to an air outlet temperature of about 35° C.–40° C. The extended release coating solution was sprayed on the cores. Upon completion the heating was discontinued but the air supply was maintained for about 10 minutes in order to dry the tablets. The coated cores were extracted from the apparatus and stored.

The coated cores were placed again in the coating pan (Glatt GC 750) and heated with warm air to an air outlet temperature of about 45° C.–50° C. The drug coating solution was sprayed on the coated cores. Upon completion the heating was discontinued but the air supply was maintained for about 10 minutes in order to dry the tablets. The drug coated cores were extracted from the apparatus and stored.

The drug coated cores were placed again in the coating pan (Glatt GC 750) and heated with warm air to an air outlet temperature of about 45° C.–50° C. The seal coating solution was sprayed on the drug coated cores. Upon completion the heating was discontinued but the air supply was maintained for about 10 minutes in order to dry the tablets. The tablets were extracted from the apparatus and stored.

We claim:

1. A four-part tablet comprising:
   (a) an extended release matrix core comprising pseudoephedrine hydrochloride as the active ingredient, a hydrophilic polymer selected from the group consisting of hydroxypropyl methyl cellulose, hydroxypropyl cellulose and hydroxyethyl cellulose as matrix material and a solid diluent;
   (b) an extended release coating;
   (c) a drug coating comprising astemizole and pseudoephedrine hydrochloride as active ingredients and a hydrophilic polymer selected from the group consisting of hydroxypropyl methyl cellulose, hydroxypropyl cellulose and hydroxyethyl cellulose; and
   (d) a seal coating,
   wherein the proportions of pseudoephedrine in the core and in the drug coating are selected so as to provide an initial burst of pseudoephedrine from the drug coating followed by sustained release of pseudoephedrine from the core whereby effective pseudoephedrine plasma concentrations are reached within one hour and are maintained for about 24 hours.

2. A tablet according to claim 1 wherein 75% of the available pseudoephedrine hydrochloride is in the core and the remaining 25% in the drug coating.

3. A tablet according to claim 1 wherein the core comprises about 60 to 240 mg pseudoephedrine hydrochloride and the drug coating comprises about 20 to 80 mg pseudoephedrine hydrochloride and about 5 to 20 mg astemizole.

4. A tablet according to claim 1 wherein the hydrophilic polymer is hydroxypropyl methylcellulose having a viscosity of about 15000 mPa·s and the solid diluent is lactose.

5. A tablet according to claim 1 wherein the extended release coating comprises ethylcellulose together with hydroxypropyl methylcellulose.

6. A tablet according to claim 1 wherein the drug coating comprises the active ingredients astemizole and pseudoephedrine hydrochloride suspended in said hydrophilic polymer.

7. A tablet according to claim 6 wherein the drug coating further comprises a plasticizer and a surfactant.

8. A tablet according to claim 1 wherein the seal coating comprises said hydrophilic polymer and a plasticizer.

9. A tablet according to claim 1 comprising
   (a) in the core
      180 mg pseudoephedrine hydrochloride
      142.65 mg lactose
      9 mg polyvidone
      1.35 mg colloidal silica
      117 mg hydroxypropyl methylcellulose having a viscosity of 15000 mPa·s
      4.5 mg magnesium stearate
   (b) in the extended release coating
      8 mg ethylcellulose having a viscosity of 20 mPa·s
      2 mg hydroxypropyl methylcellulose having a viscosity of 5 mPa·s
      2 mg PEG 400
   (c) in the drug coating:
      60 mg pseudoephedrine hydrochloride
      10 mg astemizole
      70 mg hydroxypropyl methylcellulose having a viscosity of 5 mPa·s
      16.8 mg PEG 400
      0.3 mg polysorbate 80; and
   (d) in the seal coating:
      8 mg hydroxypropyl methylcellulose having a viscosity of 5 mPa·s
      2 mg propylene glycol.

* * * * *